United States Patent
Cavezza et al.

(10) Patent No.: US 7,807,695 B2
(45) Date of Patent: Oct. 5, 2010

(54) COSMETIC USE OF PIPERIDINE DERIVATIVES

(75) Inventors: Alexandre Cavezza, Pavillon Sous Bois (FR); Michel Neuwels, Waterloo (BE)

(73) Assignee: L'Oreal, Paris (FR)

( * ) Notice: Subject to any disclaimer, the term of this patent is extended or adjusted under 35 U.S.C. 154(b) by 479 days.

(21) Appl. No.: 11/629,196

(22) PCT Filed: May 16, 2005

(86) PCT No.: PCT/EP2005/006333

§ 371 (c)(1),
(2), (4) Date: Jul. 16, 2007

(87) PCT Pub. No.: WO2005/123678

PCT Pub. Date: Dec. 29, 2005

(65) Prior Publication Data

US 2008/0090866 A1 Apr. 17, 2008

(30) Foreign Application Priority Data

Jun. 15, 2004 (FR) .................................. 04 51273

(51) Int. Cl.
*A61K 31/435* (2006.01)
*A61Q 19/08* (2006.01)
(52) U.S. Cl. ...................... 514/315; 514/317
(58) Field of Classification Search .................. 514/315
See application file for complete search history.

(56) References Cited

FOREIGN PATENT DOCUMENTS

| EP | 1 053 745 | 11/2000 |
|----|-----------|---------|
| EP | 1 405 633 | 4/2004 |
| WO | 95 24390 | 9/1995 |
| WO | 2004 056809 | 7/2004 |

OTHER PUBLICATIONS

U.S. Appl. No. 11/631,391, filed Dec. 29, 2006, Cavezza, et al.
U.S. Appl. No. 12/607,824, filed Oct. 28, 2009, Cavezza, et al.

*Primary Examiner*—Sreeni Padmanabhan
*Assistant Examiner*—Sahar Javanmard
(74) *Attorney, Agent, or Firm*—Oblon, Spivak, McClelland, Maier & Neustadt, L.L.P.

(57) ABSTRACT

The present invention relates to the cosmetic use, as an agent for combating wrinkles, especially expression wrinkles, and/or for dencontracting the skin and/or relaxing the features, of at least one piperidine derivative chosen from the compounds of formula (I):

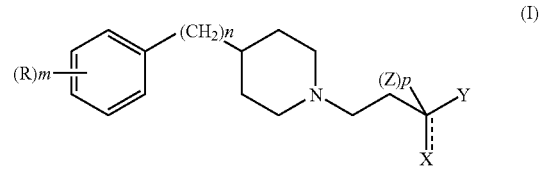

and the salts and optical isomers thereof.

The invention also relates to novel piperidine derivatives and also to cosmetic compositions containing them.

17 Claims, No Drawings

COSMETIC USE OF PIPERIDINE DERIVATIVES

The present invention relates to the cosmetic use, as an agent for combating wrinkles, especially expression wrinkles, and/or for decontracting the skin and/or relaxing the features, of at least one piperidine derivative of given formula. The invention also relates to a novel family of piperidine derivatives and to cosmetic compositions containing them.

Women, and even men, currently have a tendency to wish to look youthful for as long as possible and consequently seek to fade out the age marks on the skin, which are reflected in particular by wrinkles and fine lines. In this respect, advertising and the fashion world report about products intended to keep the skin radiant and wrinkle-free for as long as possible, which are signs of youthful skin, and all the more so since the physical appearance acts on the psyche and/or on the morale.

Hitherto, wrinkles and fine lines were treated using cosmetic products containing active agents acting on the skin, for example by improving its cell renewal or alternatively by promoting the synthesis, or by preventing the degradation of the elastic fibres thereof of which skin tissue is composed.

Although these treatments make it possible to act on the wrinkles and fine lines caused by chronological or intrinsic ageing, and also on those caused by photoageing, they have no effect on expression wrinkles which require an intervention on the muscular contractile component (via muscle-relaxing agents) or dermal contractile component (via dermo-decontracting agents) of wrinkles.

Specifically, expression wrinkles are the result of mechanisms different from those that generate the wrinkles caused by ageing.

Specifically, they are produced due to the effect of the strain exerted on the skin by the skin muscles that allow facial expressions. Depending on the shape of the face, the frequency of facial expressions and possible tics, they may appear even from childhood. Age, and also certain environmental factors such as exposure to sunlight, do not play a part in generating them, but may make them deeper and permanent.

Expression wrinkles are characterized by the presence of grooves around the orifices formed by the nose (nasal grooves), the mouth (perioral wrinkles and "sour-face" wrinkles) and the eyes (crow's-feet wrinkles), around which are the skin muscles, and also between the eyebrows (glabella wrinkles or lion wrinkles) and on the forehead.

Hitherto, the only means commonly used for acting on expression wrinkles is botulinum toxin, which is especially injected into the wrinkles of the glabella which are wrinkles between the eyebrows (see J. D. Carruters et al., *J. Dermatol. Surg. Oncol.*, 1992, 18, pp. 17-21).

The Applicant has also proposed various compounds capable of affording a muscle-relaxing effect when they are applied topically to the skin thus making it possible to act on expression wrinkles via another route. Among these compounds that may especially be mentioned are antagonists of the receptors associated with the calcium channels, such as verapamil (FR-2 793 681), and in particular manganese and its salts (FR-2 809 005) and alverine (FR-2 798 590); and agonists of the receptors associated with the chlorine channels including glycine (EP-0 704 210) and certain extracts of *Iris pallida* (FR-2 746 641); and sapogenins (EP-1 352 643).

Along with these muscle-relaxing agents, the Applicant has described various dermo-decontracting compounds and in particular amine compounds (EP-1 405 633).

However, there is still a need for other effective compounds for smoothing or fading out wrinkles, in particular expression wrinkles.

The Applicant has now discovered surprisingly, that certain piperidine derivatives can satisfy this need.

Some of these compounds have already been described as antibacterial agents (Varma, Rajendra S. et al., Synthesis and antibacterial activity of certain beta-aminoketones, *Journal of Pharmaceutical Sciences*, 57 (7), 1251-3, 1968) or as narcotic antagonists and anti-inflammatory agents in particular (Collino F. et al., Mannich ketobases with narcotic-antagonistic activity, *Bolletino Chimico Fazrmaceutico*, Societa Editoriale Farmaceutica, Milano, Vol. 122, No. 8, August 1983). Yet others have been described as chemokine receptor modulators, which may especially be used topically to treat various skin conditions such as psoriasis (WO 2004/056809).

However, it has never yet been suggested to use these compounds for cosmetic purposes, in particular for smoothing out wrinkles.

One subject of the present invention is thus the cosmetic use, as an agent for combating wrinkles especially expression wrinkles, and/or for decontracting the skin and/or relaxing the features, of at least one piperidine derivative chosen from the compounds of formula (I):

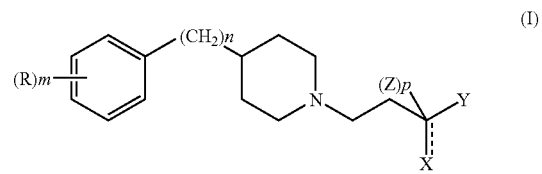

in which:
R denotes a halogen or a radical chosen from a $C_1$-$C_6$ alkyl radical, a group OR', a group NR'R", a $CF_3$ group, a group NHCOR'R" or a group CONR'R";
X denotes an oxygen atom, a hydroxyl group or a hydrogen atom;
Y denotes a phenyl group optionally substituted with at least one radical R as defined above; or a linear or branched $C_1$-$C_{17}$ alkyl or alkenyl radical optionally substituted with at least one group OR', COOR', =O, NR'R", NHCOR'R" or CONR'R" or with a phenyl group optionally substituted with at least one radical R as defined above;
Z denotes a hydrogen atom or a phenyl group optionally substituted with at least one radical R as defined above; or a linear or branched $C_1$-$C_{17}$ alkyl or alkenyl radical, optionally substituted with at least one group OR', COOR', =O, NR'R", NHCOR'R" or CONR'R";

it being understood that when X and Z each denote a hydrogen atom and when Y denotes an alkyl or alkenyl radical, the said radical contains at least 5 carbon atoms,
in which R' and R" denote, independently of each other, a hydrogen atom or a $C_1$-$C_6$ alkyl radical,
m ranges from 0 to 5;
n ranges from 2 to 5;
p is 0 when X is an oxygen atom and 1 in the other cases,
and the salts and optical isomers thereof.

A subject of the invention is also a cosmetic process for treating wrinkled skin, in particular skin of the face and/or the forehead, comprising the topical application to the said skin of a composition comprising, in a physiologically acceptable medium, at least one piperidine derivative as defined above.

Insofar as some of the piperidine derivatives of formula (I) are novel per se, a subject of the invention is also these novel piperidine derivatives, characterized in that they are chosen from the compounds of formula (I) above and the salts and optical isomers thereof, it being understood that when Y denotes an optionally substituted phenyl group, X is a hydrogen atom.

A subject of the invention is also a composition containing, in a physiologically acceptable medium, at least one of the novel piperidine derivatives as defined above.

In formula (I) the alkyl groups may be chosen especially, depending on the case, from the following groups: methyl, ethyl, n-propyl, isopropyl, n-butyl, isobutyl, tert-butyl, pentyl, hexyl, heptyl, octyl, nonyl, decyl, undecyl, dodecyl, myristyl and palmityl.

In addition, in the context of this application, the term "alkenyl" means radicals possibly comprising one or more conjugated or non-conjugated double bonds. They may be chosen especially, depending on the case, from the following groups: vinyl, allyl butenyl or pentenyl.

Radicals R that are preferred in formula (I) are methoxy ($OCH_3$) and trifluoromethyl ($CF_3$) radicals.

Salts of the compound of formula (I) that may be mentioned include the salts obtained by addition of the compound of formula (I) to a mineral acid, chosen especially from hydrochloric acid, sulfuric acid and phosphoric acid, or to an organic acid, chosen in particular from acetic acid, propionic acid, succinic acid, fumaric acid, lactic acid, glycolic acid, citric acid and tartaric acid.

Preferably, the piperidine derivative according to the invention is such that m ranges from 0 to 3 and m is preferably equal to 0, and/or n is equal to 2 or 3 and n is preferably equal to 3.

In addition, according to a first advantageous embodiment of the invention:

X is a hydrogen atom,
Y is a phenyl group,
m is equal to 0,
n is equal to 3,
p is equal to 1, and
Z is a hydrogen atom.

According to a second advantageous embodiment of the invention:

X is an oxygen atom,
Y is a linear or branched $C_1$-$C_{10}$ alkyl radical,
m is equal to 0,
n is equal to 3, and
p is equal to 0.

According to a third advantageous embodiment of the invention:

X is a hydroxyl group,
Y is a linear or branched $C_1$-$C_{10}$ alkyl radical,
m is equal to 0,
n is equal 3,
p is equal to 1, and
Z is a linear or branched $C_1$-$C_{10}$ alkyl radical.

In these second and third embodiments of the invention, the alkyl radicals are preferably linear alkyl radicals. They preferably contain from 3 to 7 carbon atoms and preferentially 5 carbon atoms.

The compounds of formula (I) may be prepared especially according to the following reaction scheme:

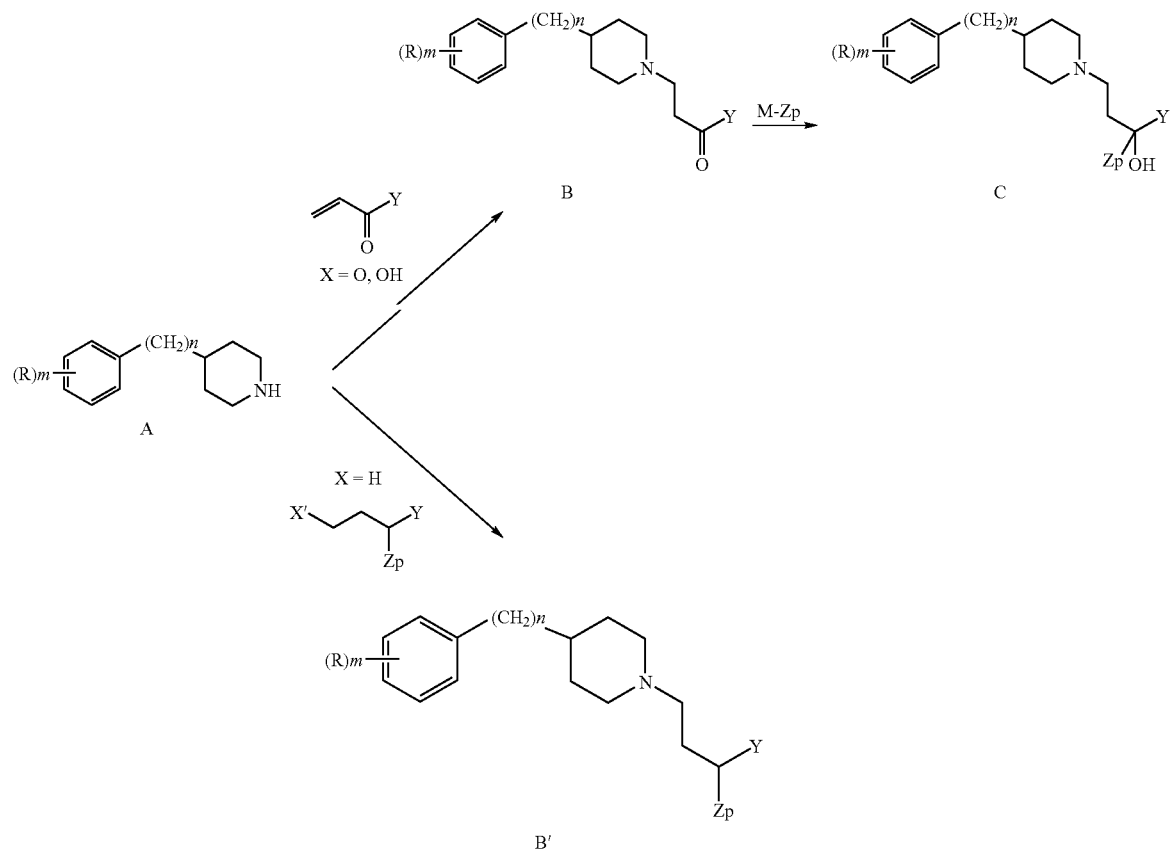

M = Li, MgBr, ZnI
X' = halogen, sulfonate by reaction of the substituted piperidine A (1 eq) with 1 equivalent of α,β-unsaturated ketone in ethanol, at room temperature. The product B may be worked up and purified on a column of silica. Alternatively, product A (1 eq) may be reacted with the corresponding halo or sulfonate radical (1 eq) in the presence of $K_2CO_3$ in refluxing acetonitrile overnight. The product obtained B' may be worked up and purified on a column of silica.

To obtain C, 1 equivalent of metallic derivative Zp (organomagnesium, organolithium or organozinc agent) may be reacted with 1 equivalent of compound B, in anhydrous THF, under nitrogen, at room temperature. The product C thus obtained may be worked up and purified on a column of silica.

The amount of piperidine derivative that may be used according to the invention obviously depends on the desired effect and may thus vary within a wide range.

To give an order of magnitude these derivatives may be used in an amount representing from 0.01% to 10% of the total weight of the composition, preferably in an amount representing from 0.05% to 5% of the total weight of the composition and more preferably in an amount representing from 0.1% to 2% of the total weight of the composition.

The composition used according to the invention is suitable for topical application to the skin and thus contains a physiologically acceptable medium, i.e. a medium that is compatible with the skin and optionally with its integuments (eyelashes, nails and hair) and/or mucous membranes. This medium is advantageously cosmetically acceptable, i.e. it does not cause any itching, stinging or redness liable to put the user off the composition and it has a pleasant appearance, odour and feel.

This composition may be in any presentation form normally used in cosmetics, and it may especially be in the form of an optionally gelled solution, a dispersion of the lotion type, optionally a two-phase lotion, an emulsion obtained by dispersing a fatty phase in an aqueous phase (O/W emulsion) or conversely (W/O emulsion), or a triple emulsion (W/O/W or O/W/O emulsion) or a vesicular dispersion of ionic and/or nonionic type. These compositions are prepared according to the usual methods A composition in the form of an oil-in-water emulsion is preferably used according to this invention.

This composition may be more or less fluid and may have the appearance of a white or coloured cream, an ointment, a milk, a lotion a serum, a paste or a mousse. It may optionally be applied in the form of an aerosol. It may also be in solid form, in particular in the form of a stick. It may be used as a care product, and/or as a makeup product for the skin.

In a known manner, the composition used according to the invention may also contain adjuvants that are common in cosmetics such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants are those conventionally used in the field under consideration, and, for example, from 0.01% to 20% relative to the total weight of the composition. Depending on their nature, these adjuvants may be introduced into the fatty phase, into the aqueous phase, or into lipid vesicles. In any case, these adjuvants, and also the proportions thereof, will be chosen so as not to harm the desired properties of the compounds according to the invention.

When the composition used according to the invention is an emulsion, the proportion or the fatty phase may range from 5% to 80% by weight and preferably from 5% to 50% by weight relative to the total weight of the composition. The oils, emulsifiers and co-emulsifiers used in the composition in emulsion form are chosen from those conventionally used in the field under consideration. The emulsifier and co-emulsifier are present in the composition in a proportion ranging from 0.3% to 30% by weight and preferably from 0.5% to 20% by weight relative to the total weight of the composition.

As oils which may be used in the invention mention may be made of mineral oils (liquid petroleum jelly), oils of plant origin (avocado oil or soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax or ozokerite) may also be used as fatty substances.

As examples of emulsifiers and co-emulsifiers that may be used in the invention, mention may be made of fatty acid esters of polyethylene glycol such as PEG-100 stearate, and fatty acid esters of glycerol such as glyceryl stearate.

Hydrophilic gelling agents/thickeners that may be mentioned in particular include carboxyvinyl polymers (carbomer), acrylic copolymers such as acrylate/alkylacrylate copolymers, polyacrylamides, polysaccharides, natural gums and clays, and lipophilic gelling agents/thickeners that may be mentioned include modified clays, for instance bentones, metal salts of fatty acids and hydrophobic silica.

As active agents, it will be advantageous to introduce into the composition used according to the invention at least one compound chosen from: desquamating agents; moisturizers; depigmenting or propigmenting agents; antiglycation agents; NO-synthase inhibitors; agents for stimulating the synthesis or dermal or epidermal macromolecules and/or for preventing their degradation; agents for stimulating the proliferation of fibroblasts and/or keratinocytes or for stimulating the differentiation of keratinocytes; other muscle-relaxing agents and/or dermo-decontracting agents; tensioning agents; antipollution agents and/or free-radical scavengers; agents acting on the capillary circulation; agents acting on the energy metabolism of cells; and mixtures thereof.

Examples of such additional compounds are: retinol and its derivatives such as retinyl palmitate; ascorbic acid and its derivatives such as magnesium ascorbyl phosphate and ascorbyl glucoside; tocopherol and its derivatives such as tocopheryl acetate; nicotinic acid and its precursors such as nicotinamide; ubiquinone; glutathione and its precursors such as L-2-oxothiazolidine-4-carboxylic acid; plant extracts and especially plant proteins and hydrolysates thereof, and also plant hormones; marine extracts such as algal extracts; bacterial extracts; sapogenins such as diosgenin and extracts of wild yam containing it; ceramides; hydroxy acids such as salicylic acid and 5-n-octanoylsalicylic acid; resveratrol; oligopeptides and pseudodipeptides and acyl derivatives thereof; manganese and magnesium salts, in particular the gluconates; and mixtures thereof.

As mentioned previously, the composition according to the invention may also contain UVA-active and/or UVB-active photoprotective agents, in the form of organic or mineral compounds, the latter optionally being coated to make them hydrophobic.

The organic photoprotective agents may be chosen especially from: anthranilates, in particular menthyl anthranilate; benzophenones, in particular benzophenone-1, benzophenone-3, benzophenone-5, benzophenone-6, benzophenone-8, benzophenone-9, benzophenone-12 and, preferably, benzophenone-3 (oxybenzone) or benzophenone-4 (Uvinul MS40 available from BASF; benzylidenecamphors, in particular 3-benzylidenecamphor, benzylidenecamphorsulphonic acid, camphor benzalkonium methosulphate, polyacrylamidomethylbenzylidenecamphor, terephthalylidenedicamphorsulphonic acid and, preferably, 4-methylbenzylidenecamphor (Eusolex 6300 available from Merck);

benzimidazoles, in particular benzimidazilate (Neo Heliopan AP available from Haarmann & Reimer), or phenylbenzimidazolesulphonic acid (Eusolex 232 available from Merck); benzotriazoles, in particular drometrizole trisiloxane, or methylenebisbenzotriazolyltetramethylbutylphenol (Tinosorb M available from Ciba); cinnamates, in particular cinoxate, DEA methoxycinnamate, diisopropyl methylcinnamate, glyceryl ethylhexanoate dimethoxycinnamate, isopropyl methoxycinnamate, isoamyl cinnamate and, preferably, ethocrylene (Uvinul N35 available from BASF), octyl methoxycinnamate (Parsol MCX available from Hoffmann La Roche), or octocrylene (Uvinul 539 available from BASF); dibenzoylmethanes, in particular butylmethoxydibenzoylmethane (Parsol 1789); imidazolines, in particular ethylhexyl dimethoxybenzylidene dioxoimidazoline; PABAs, in particular ethyl dihydroxypropyl PABA, ethylhexyldimethyl PAPA, glyceryl PABA, PABA, PEG-25 PABA and, preferably, diethylhexylbutamidotriazone (Uvasorb HEB available from 3V Sigma), ethylhexyltriazone (Uvinul TEA available from BASF) or ethyl PABA (benzocaine); salicylates, in particular dipropylene glycol salicylate, ethylhexyl salicylate, homosalate or TEA salicylate; triazines, in particular anisotriazine (Tinosorb S available from Ciba) drometrizole trisiloxane.

The mineral photoprotective agents preferably consist of zinc oxide and/or titanium dioxide, preferably of nanometric size, optionally coated with alumina and/or stearic acid.

The composition according to the invention is advantageously intended to be applied to the areas of the face and/or forehead that are marked with expression wrinkles, and/or on individuals with expression wrinkles.

The wrinkles concerned are preferably those lying radially around the mouth and/or the eyes, in particular the crow's-feet wrinkles, and/or lying on the forehead, in particular the "lion" wrinkle, located in the glabella, in between the eyebrows and/or lying horizontally on the forehead.

The invention will now be illustrated with the non-limiting examples that follow. In these examples, the amounts are indicated as percentages by weight.

EXAMPLES

Example 1

Synthesis of 1,4-bis(3-phenylpropyl)-piperidine

This compound was prepared according to the following reaction scheme:

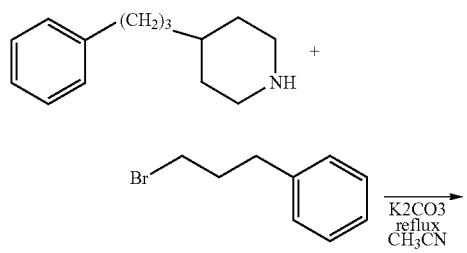

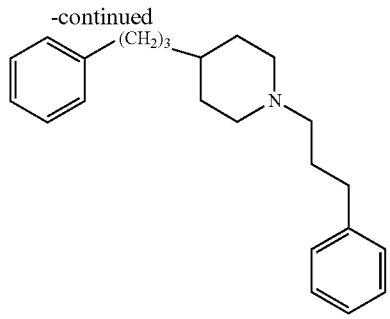

3-Phenylpropylpiperidine (1 eq) was reacted with 3-phenylbromopropane (1 eq) in the presence of $K_2CO_3$ in refluxing acetonitrile over night. The product obtained was worked up and purified on a column of silica. The 500 MHz $^1$H NMR is in accordance with the expected structure.

Example 2

Synthesis of 1-[4-(3-phenylpropyl)piperidin-1-yl]octan-3-one

This compound was prepared according to the following reaction scheme:

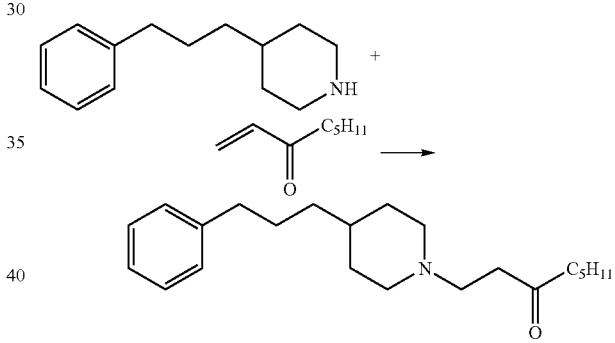

1 equivalent of 4-(3-phenylpropyl)piperidine was reacted with 1 equivalent of 1-octen-3-one in ethanol, at room temperature. The product was worked up and purified on a column of silica. The results of the NMR and mass spectrometry analyses were in accordance with the expected structure.

Example 3

Synthesis of 6-{2-[4-(3-phenylpropyl)-piperidin-1-yl]ethyl}undecan-6-ol

This compound was prepared from the compound of Example 2, according to the following reaction scheme:

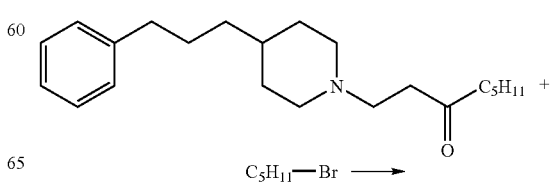

-continued

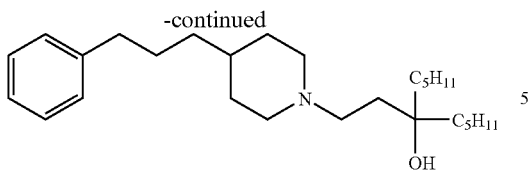

1 equivalent of pentylmagnesium bromide was reacted with 1 equivalent of the compound obtained in Example 2, in anhydrous THF, under nitrogen, at room temperature. The product thus obtained was worked up and purified on a column of silica. The results of the NMR and mass spectrometry analyses were in accordance with the expected structure.

Example 4

Demonstration of the Muscle-Relaxing Effect of the Derivatives According to the Invention The compound of Example 1 was tested on a model of nerve/muscle coculture, which makes it possible to recreate a motor arc by innervating human striated muscle cells with explants of rat embryonic rachidian ganglia and spinal cord.

This test is predictive of an anti-wrinkle effect, as demonstrated by the Applicant in the case of diazepam, which inhibited muscle fibre contractions in this model and whose anti-wrinkle activity has been demonstrated in vivo.

a) Protocol

Human muscle cells, obtained from samples of striated muscle from healthy donors, are inoculated into wells of cross section 1.8 cm$^2$ (24-well culture dishes). After culturing for ten days, these cells form a monolayer and fuse. At this stage, explants of embryonic spinal cord from a 13 day-old rat, containing the rachidian ganglia, are placed on the culture.

The growth of the neurites is visible beyond the spinal cord explant after one day of culture. The first contractions of the muscle fibres are observed after five to six days of coculture, and after three weeks all the muscle fibres in the region of the explants contract.

The cocultures are used after 21 days, when the muscle fibres are striated and contain mature differentiated neuromuscular junctions.

A muscle fibre showing regular contractions (at least 60 contractions per minute) is then selected from three different culture wells and the number of contractions is counted over 30 seconds. The test compound, diluted in DMSO, is then incubated for 60 seconds in these wells, at a concentration of $10^{-5}$ M. At the end of incubation, the number of contractions is again counted over 30 seconds. The test is performed in triplicate.

b) Results

One minute after adding the test compound to the wells the contractions of the fibre represent only 55% of its contractions before addition of the compound.

This compound therefore inhibits striated muscle contractions and can thus be used to relax the features of the face and to smooth out expression wrinkles.

Example 5

Cosmetic Composition

This composition is prepared in a conventional manner for a person skilled in the art. The amounts given in this example are indicated in weight percentages.

| | |
|---|---|
| Compound of Example 1 | 0.10% |
| Stearic acid | 3.00% |
| Mixture of glyceryl monostearate and polyethylene glycol stearate (100 EO) | 2.50% |
| Polyethylene glycol stearate (20 EO) | 1.00% |
| Cyclopentadimethylsiloxane | 10.00% |
| Fillers | 3.00% |
| Plant oils | 7.00% |
| Synthetic oils | 6.00% |
| Preserving agents | 1.20% |
| Oxyethylenated dimethylsiloxane (16 EO) containing methoxy end groups | 1.00% |
| Silicone gum | 0.20% |
| Acrylic copolymer as an inverse emulsion (Simulgel 600 from SEPPIC) | 1.70% |
| Stearyl alcohol | 1.00% |
| Water qs | 100% |

This cream is intended to be applied to the face and the forehead to relax the features and to decontract facial skin.

The invention claimed is:

1. A method for combating wrinkles in a composition containing human skin comprising applying at least one piperidine compound, or its salt, of formula (I):

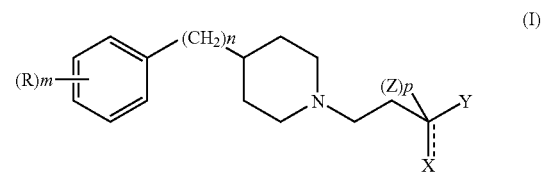

to the wrinkles a content of the piperidine compound in the composition is 0.01 to 10% of the total weight of the composition;
wherein:
R is selected from the group consisting of a halogen, a $C_1$-$C_6$ alkyl radical, an OR' group, an NR'R" group, a $CF_3$ group, a NHCOR'R" group, and a CONR'R" group;
X is selected from the group consisting of an oxygen atom, a hydroxyl group, and a hydrogen atom;
Y is selected from the group consisting of a phenyl group a linear $C_1$-$C_{17}$ alkyl radical, a branched $C_1$-$C_{17}$ alkyl radical, a linear $C_1$-$C_{17}$ alkenyl radical, and a branched $C_1$-$C_{17}$ alkenyl radical;
Z is selected from the group consisting of a hydrogen atom, a phenyl group, a linear $C_1$-$C_{17}$ alkyl radical, a branched $C_1$-$C_{17}$ alkyl radical, a linear $C_1$-$C_{17}$ alkenyl radical, and a branched $C_1$-$C_{17}$ alkenyl radical;
with the proviso that when X and Z each are a hydrogen atom, p=1, and when Y is an alkyl or alkenyl radical, the alkyl or alkenyl radical comprises at least 5 carbon atoms,
wherein R' and R", independently of each other, are selected from the group consisting of a hydrogen atom and a $C_1$-$C_6$ alkyl radical,
m ranges from 0 to 5;
n ranges from 2 to 5; and
p is 0 when X is an oxygen atom and 1 in the other cases.

2. The method of claim 1, comprising a salt of formula (I), wherein the salt is obtained by addition of the compound of formula (I) to a mineral acid selected from the group consisting of hydrochloric acid, sulphuric acid, phosphoric acid, and combinations thereof.

3. The method of claim 1, comprising a salt of formula (I), wherein the salt is obtained by addition of the compound of formula (I) to an organic acid selected from the group consisting of acetic acid, propionic acid, succinic acid, fumaric acid, lactic acid, glycolic acid, citric acid, tartaric acid, and combinations thereof.

4. The method of claim 1, wherein m ranges from 0 to 3.

5. The method of claim 1, wherein n equals 2 or 3.

6. The method of claim 1, wherein:
X is a hydrogen atom,
Y is a phenyl group,
m is equal to 0,
n is equal to 3,
p is equal to 1, and
Z is a hydrogen atom.

7. The method of claim 1, wherein:
X is an oxygen atom,
Y is a linear or branched $C_1$-$C_{10}$ alkyl radical,
m is equal to 0,
n is equal to 3, and
p is equal to 0.

8. The method of claim 1, wherein:
X is a hydroxyl group,
Y is a linear or branched $C_1$-$C_{10}$ alkyl radical,
m is equal to 0,
n is equal 3,
p is equal to 1, and
Z is a linear or branched $C_1$-$C_{10}$ alkyl radical.

9. The method of claim 7, wherein Y is a linear $C_1$-$C_{10}$ alkyl radical.

10. The method of claim 7, wherein Y is a linear or branched $C_3$-$C_7$ alkyl radical.

11. The method of claim 1, wherein the human skin is located on at least one location selected from the group consisting of the face and the forehead.

12. The method of claim 11, wherein the wrinkles are expression wrinkles.

13. The method of claim 2, wherein m ranges from 0 to 3.

14. The method of claim 3, wherein m ranges from 0 to 3.

15. The method of claim 2, wherein n equals 2 or 3.

16. The method of claim 3, wherein n equals 2 or 3.

17. The method of claim 4, wherein n equals 2 or 3.

* * * * *